United States Patent [19]
Linhares et al.

[11] Patent Number: 6,030,377
[45] Date of Patent: *Feb. 29, 2000

[54] PERCUTANEOUS TRANSMYOCARDIAL REVASCULARIZATION MARKING SYSTEM

[75] Inventors: Stephen J. Linhares; Charles Christopher Negus, both of Taunton; Robert I. Rudko, Holliston; Eileen A. Woodruff, Millis, all of Mass.

[73] Assignee: PLC Medical Systems, Inc., Franklin, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/731,862

[22] Filed: Oct. 21, 1996

[51] Int. Cl.⁷ .................................................. A61N 5/06
[52] U.S. Cl. .................. 606/7; 606/15; 606/10; 600/508
[58] Field of Search ................. 606/2, 3–18; 128/898; 600/508

[56] References Cited

U.S. PATENT DOCUMENTS

| 4,448,188 | 5/1984 | Loeb . |
| 5,389,096 | 2/1995 | Aita et al. . |
| 5,725,523 | 3/1998 | Mueller ..................................... 606/16 |

*Primary Examiner*—David M. Shay
*Attorney, Agent, or Firm*—Iandiorio & Teska; Brian J. Colandreo

[57] ABSTRACT

A system and method of marking percutaneous transmyocardial revascularization channels in a human heart includes inserting a catheter system into the left ventricle of a heart, applying tissue ablative energy through the catheter to create a channel into the heart wall, and introducing an imaging medium to the heart wall proximate the channel for marking the position of that channel for imaging.

2 Claims, 10 Drawing Sheets

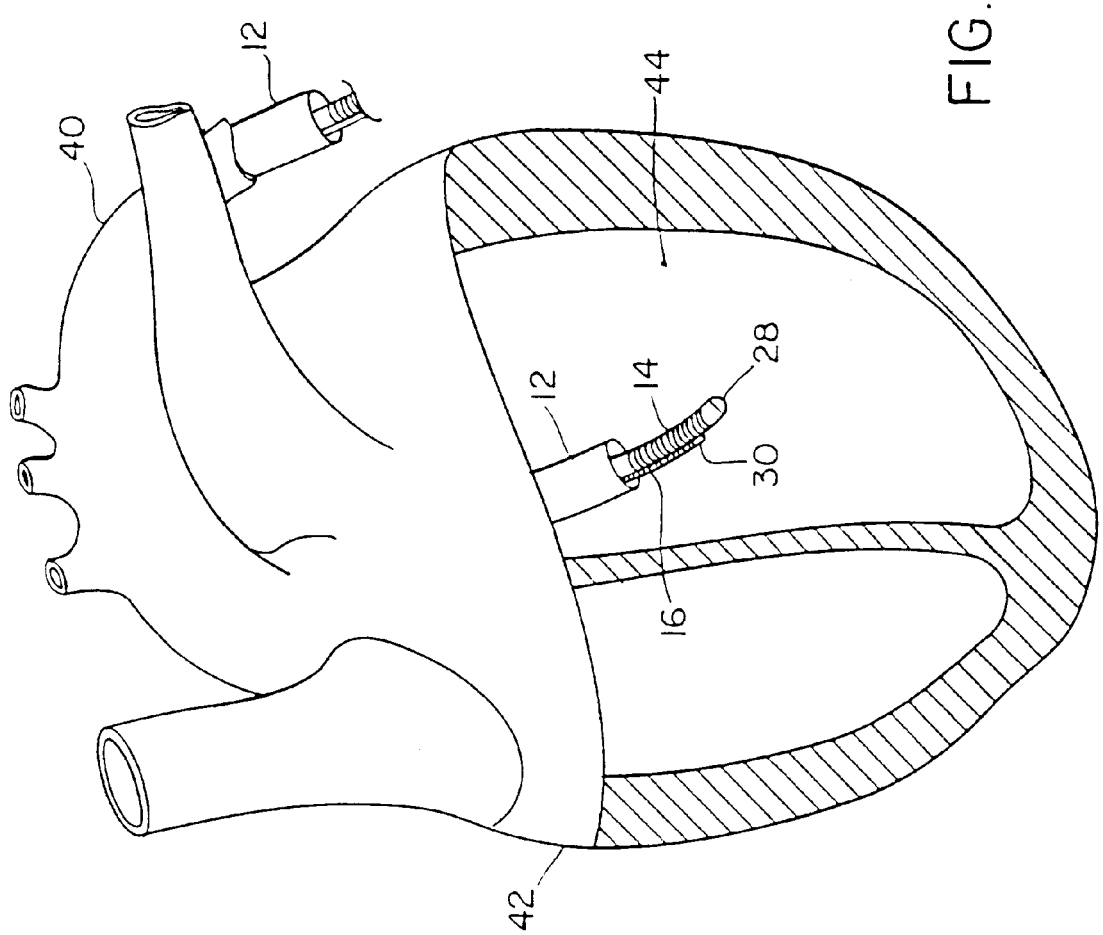

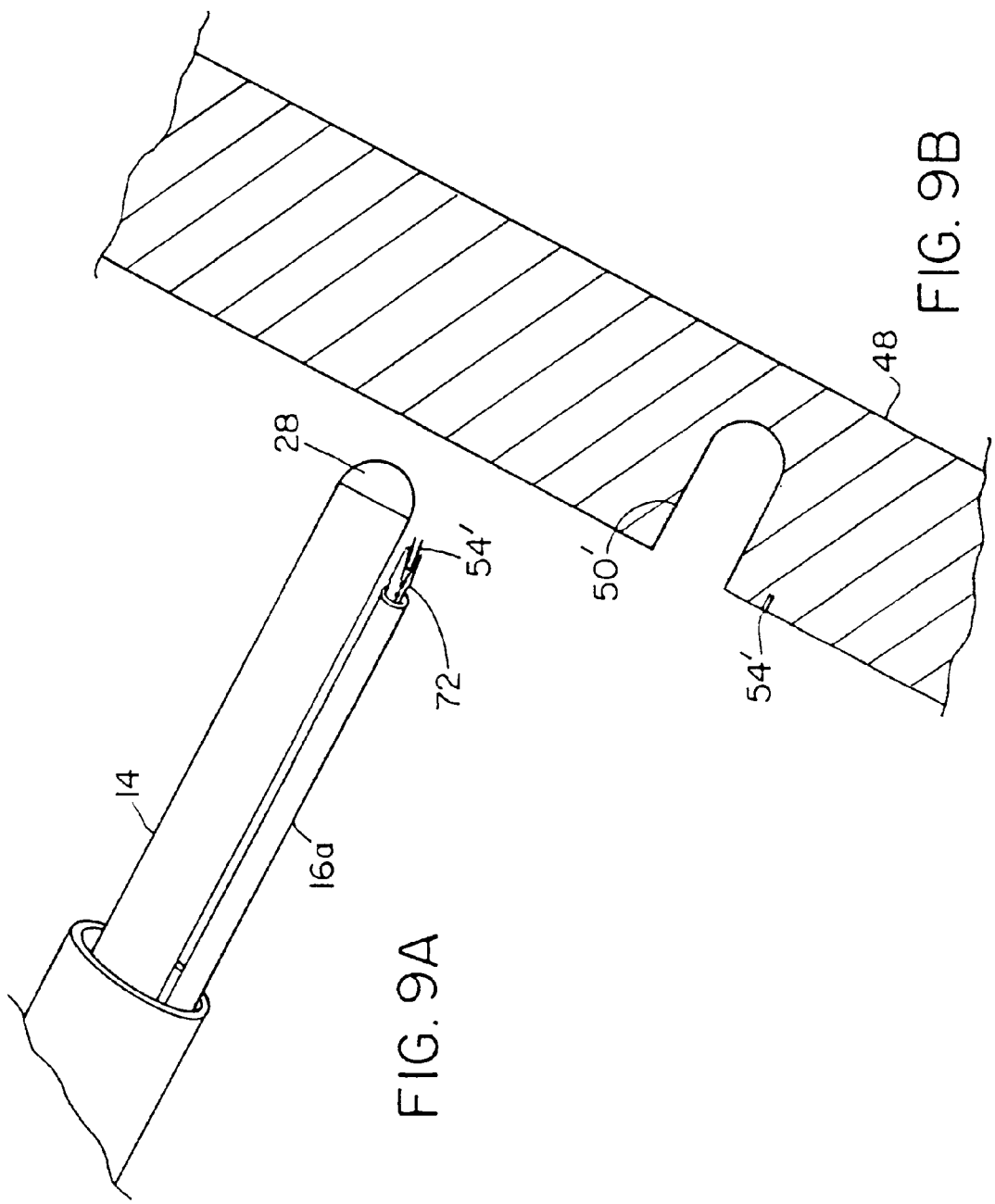

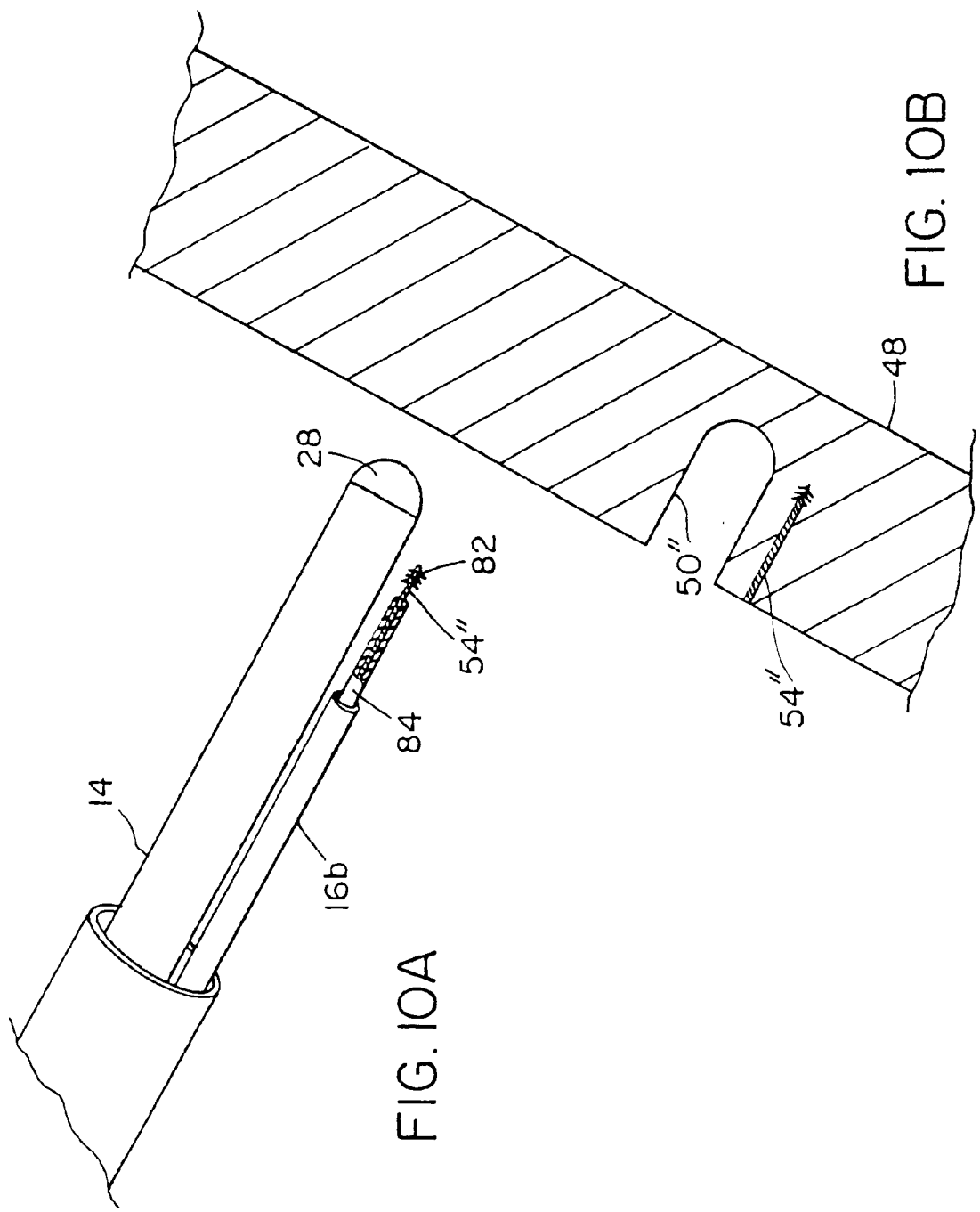

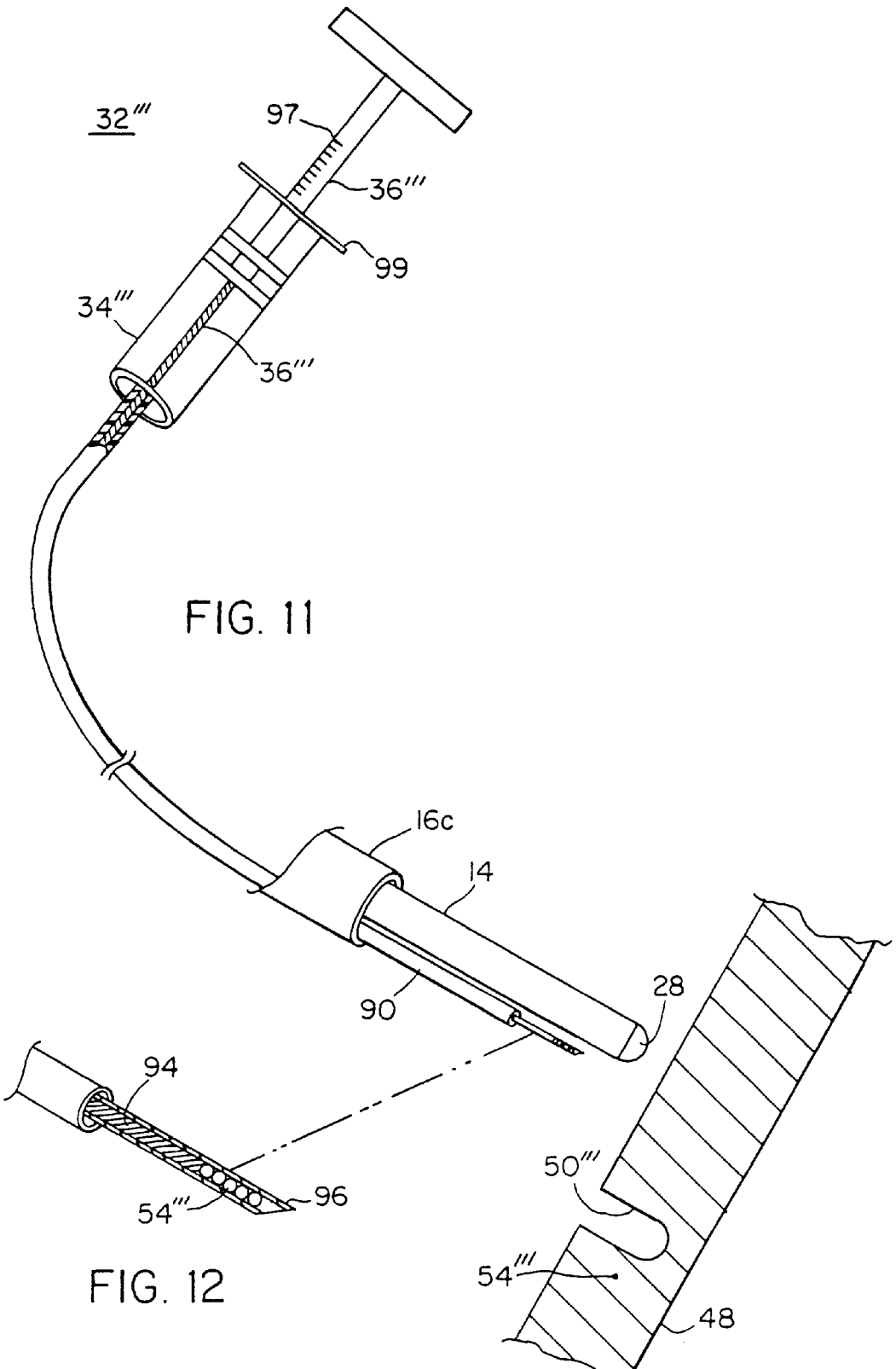

PERCUTANEOUS TRANSMYOCARDIAL REVASCULARIZATION MARKING SYSTEM

FIELD OF INVENTION

This invention relates to a percutaneous TMR channel marking system and method.

BACKGROUND OF INVENTION

Transmyocardial revascularization (TMR) is presently accomplished using a laser to create channels in the wall of the left ventricle of the heart to perfuse the ischemic myocardium, thereby supplying blood and oxygen directly to the heart muscle, instead of installing one or more bypasses or using angioplasty to overcome blocked arteries and reinstate adequate blood flow. In one approach a $CO_2$ laser is used to create channels from the outside of the heart wall to the inside. The channels heal rapidly on the outside, from digital pressure applied to the outside surfaces, leaving blind channels extending from the inside part way through the heart wall. During surgery the surgeon can see each channel and carefully choose subsequent channel sites with correct spacing between them and avoid the danger of cutting a new channel too close to an existing one. In another approach a Holmium or excimer laser supplies energy through a fiber optic element in a catheter to the inside of the left ventricle where channels are created in the heart wall from the inside toward but hopefully never reaching the outside of the wall: unlike channels cut from the outside in using a $CO_2$ laser, channels cut from the inside through to the outside using Holmium or excimer lasers do not heal easily. Thus a channel cut through to the outer wall will cause a serious leak, pouring blood into the pericardium. This requires immediate emergency action, namely, open heart surgery to suture or apply a tamponade to the hole; otherwise the patient will die within a few minutes. Since when working from the inside out using a catheter a surgeon cannot see exactly where the fiber optic element is aimed nor can he tell where the previous channels have been cut, he constantly runs the risk of cutting a new channel next to, overlapping or even right on an existing channel, which can result in accidentally cutting right through the heart wall.

SUMMARY OF INVENTION

It is therefore an object of this invention to provide a percutaneous TMR channel marking system and method.

It is a further object of this invention to provide such a percutaneous TMR channel marking system which enables a surgeon to see the existing channels using standard imaging techniques.

It is a further object of this invention to provide such a percutaneous TMR channel marking system which when cutting channels from the inside out avoids the possibility of cutting channels too close, overlapping, or right on an existing channel and avoids the possibility of cutting a channel too far and through the heart wall.

It is a further object of this invention to provide such a percutaneous TMR channel marking system which enables channels to be cut from the inside out in an organized pattern with proper placement and spacing.

It is a further object of this invention to provide such a percutaneous TMR channel marking system which creates a temporary or permanent record of the channel placement for future reference and therapy as well as autoptic analysis.

The invention results from the realization that a truly safe and effective system and method for marking percutaneous transmyocardial revascularization channels created in the heart wall can be achieved by placing an imaging medium proximate each channel to enable a surgeon to see existing channels using standard imaging techniques, and place the channels in an organized pattern with proper placement and spacing.

This invention features a percutaneous transmyocardial revascularization marking system including a catheter system for insertion into a chamber of a heart. The catheter includes a treatment catheter having its proximal end interconnected with a source of tissue ablative energy and its distal end having means for applying that energy to the heart wall to create a channel in it. The catheter also includes a marking catheter having means for introducing an imaging medium into the heart wall proximate the channel created by the treatment catheter.

In a preferred embodiment the imaging medium may include a radiopaque dye. The means for introducing may include a needle or cannula for administering the dye into the heart wall. The means for introducing may further include a source of imaging medium. That source of imaging medium may include a syringe. The imaging medium may include a metal element. The metal element may include a staple and the means for introducing may include a staple applicator. The imaging means may include a suture and the means for introducing may include a cannula for applying that suture. The imaging means may include a bead and the means for introducing may include a cannula and plunger for inserting the bead. The treatment catheter may include a fiber optic element and the source of tissue ablative energy may be a laser.

This invention also features a percutaneous transmyocardial revascularization marking system including a catheter system for percutaneous insertion into a chamber of a heart. The catheter includes a treatment catheter having its proximal end interconnected with a source of tissue ablative energy and its distal end having means for applying that energy to the heart wall to create a channel part way through it. There is a marking catheter having its proximal end interconnected with a source of imaging medium and its distal end having means for introducing an imaging medium into the heart wall proximate the channel created by the treatment catheter.

This invention also features a method of marking a percutaneous transmyocardial revascularization channel including inserting a catheter into a chamber of a heart; applying tissue ablative energy through the catheter to create a channel into the heart wall; and introducing to the heart wall proximate the channel an imaging medium for marking the position of that channel for electronic imaging.

In a preferred embodiment the method may further include aiming the catheter at a new position of the heart wall spaced from the previously marked channels, applying tissue ablative energy through the catheter to create another channel into the heart wall and introducing to the heart wall proximate the channel an imaging medium for marking the position of that channel.

DISCLOSURE OF PREFERRED EMBODIMENT

Other objects, features and advantages will occur to those skilled in the art from the following description of a preferred embodiment and the accompanying drawings, in which:

FIG. 2 is an enlarged schematic partially sectional view of a human heart with the system of FIG. 1 engaged with the left ventricle;

FIG. 9A is an enlarged three-dimensional schematic view of the tip of a marking catheter for introducing staple markers into the heart wall;

FIG. 9B is a sectional view of a portion of the heart wall after a channel has been cut and a marker staple has been installed;

FIG. 10A is a view similar to FIG. 9A showing a marker catheter for inserting marker sutures into the heart wall;

FIG. 10B is a view similar to FIG. 9B showing a marker suture installed in the wall of the heart;

FIG. 11 is a view similar to FIGS. 9A and 10A showing a marker catheter for introducing radiopaque beads into a heart wall;

FIG. 12 is an enlarged detailed partially sectional view of the tip of the marker catheter of FIG. 11 showing the plunger and a bead about to be dispensed;

FIG. 13 is a view similar to FIGS. 9B and 10B showing a heart wall with the channel cut into it and a marker radiopaque bead adjacent the channel;

Figure 1:
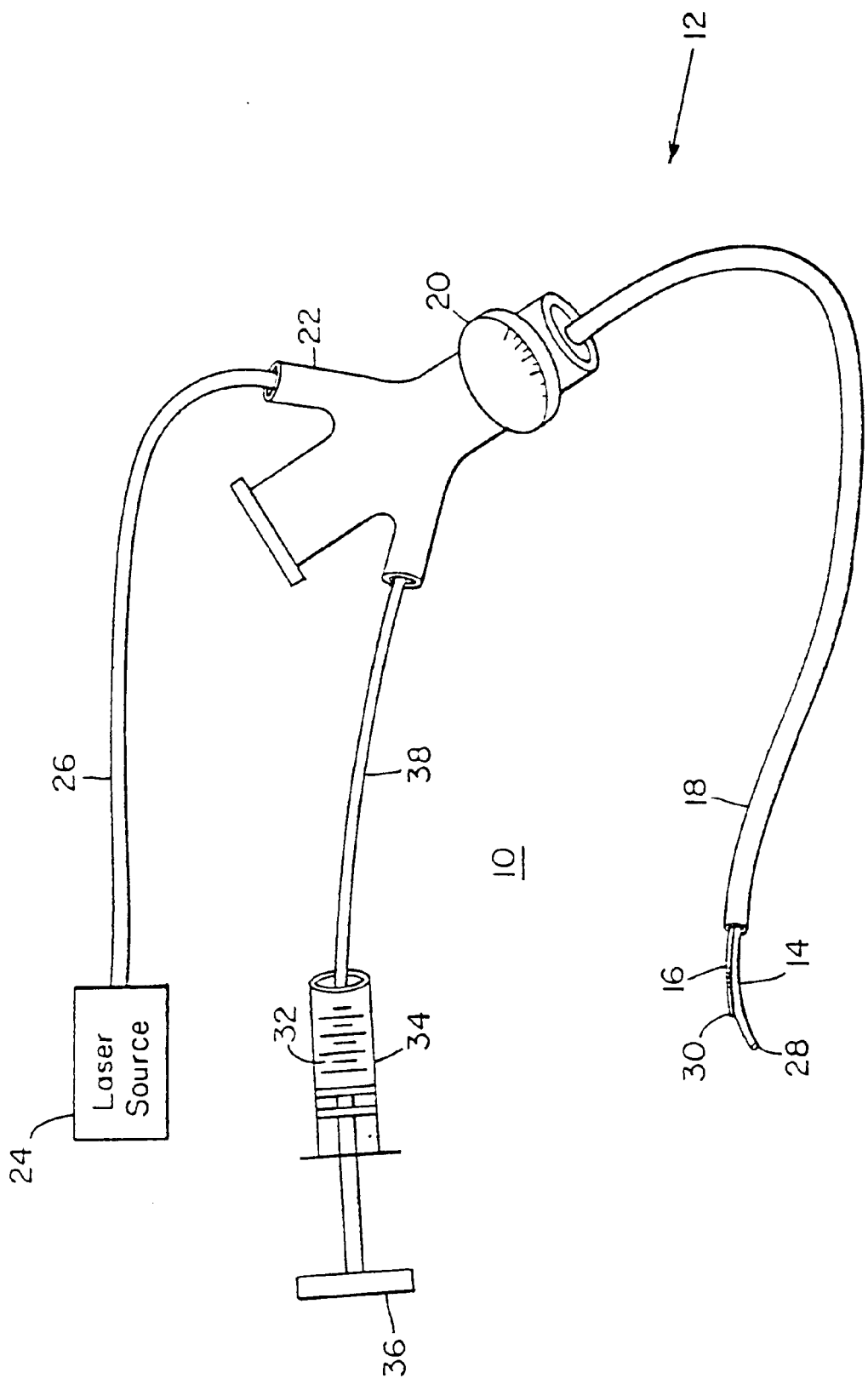
FIG. 1 is a schematic diagram of a percutaneous transmyocardial revascularization marking system according to this invention.

There is shown in FIG. 1 a percutaneous transmyocardial revascularization marking system 10 according to this invention including a catheter system 12 which includes a treatment catheter 14 and a marking catheter 16. The tip 18 of catheter system 12 is aimed or manipulated by means of knob 20 in the manner of conventional catheter control. Knob 20 is mounted on control 22 which interconnects treatment catheter 14 to a source of tissue ablative energy. In this case the source of tissue ablative energy is a laser 24 which provides the laser beam through laser catheter 26 which may for example be a fiber optic element. The laser beam is then delivered to treatment catheter 14 which may also be a fiber optic element with a lens 28 at its distal end. Marking catheter 16 may include a needle or cannula at its distal end or tip 30 for dispensing a dye which is radiopaque, or X-ray opaque, so that it may be recognized through techniques of nuclear magnetic resonance, X-ray fluoroscopy or similar imaging techniques. The dye may be injected using syringe 32 that includes a body 34 and plunger 36. The dye may be a liquid which is delivered through conduit 38 and control 22 to marking catheter 16.

Figure 4:
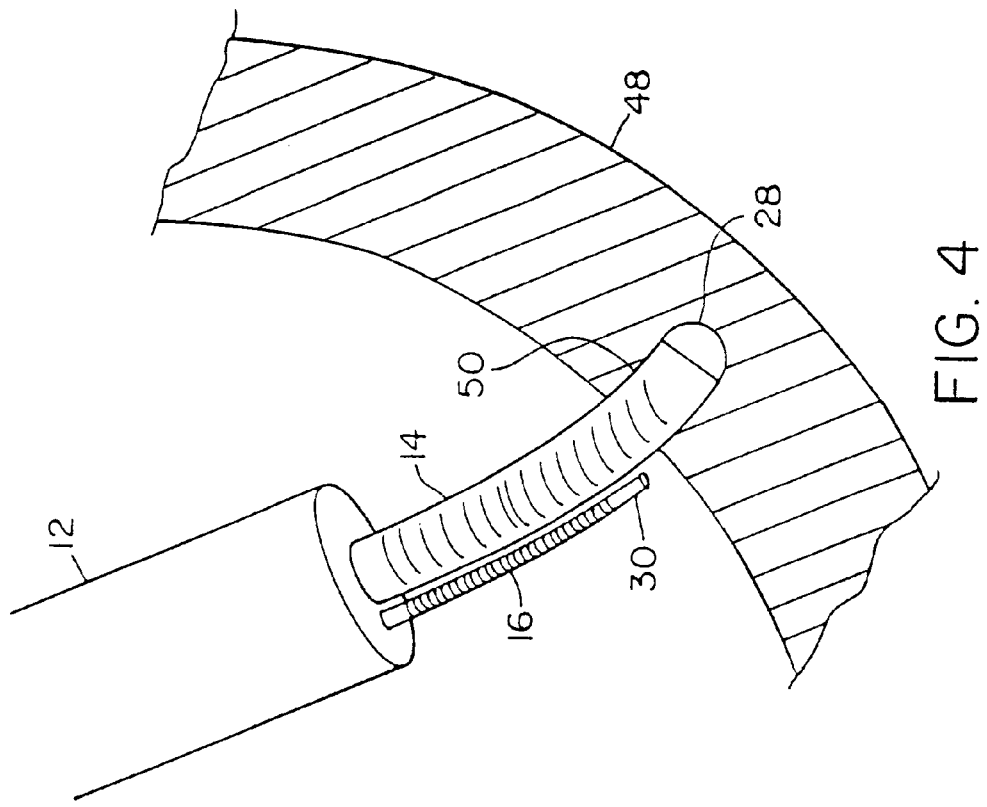
FIG. 4 is a view similar to FIG. 3 after the ablative energy has been applied and a channel has been cut into the heart wall.

Catheter system 12 is threaded through the aorta 40, FIG. 2, of human heart 42 so that the lens 28 of treatment catheter 14 and the tip 30 of marking catheter 16 are inside left ventricle 44. By manipulating knob 20 on control 22 lens 28 of treatment catheter 14 is placed against the surface 46, FIG. 3, of heart wall 48 and laser 24 is energized. This provides ablative energy at heart wall 48 and creates a channel 50, FIG. 4, in heart wall 48.

Figure 5:
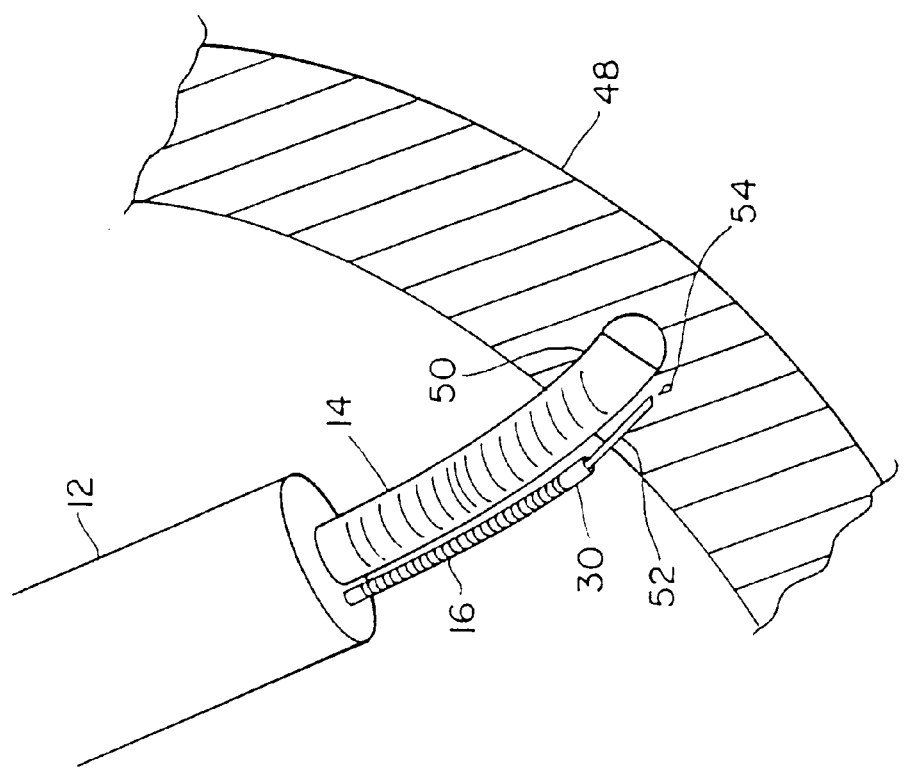
FIG. 5 is a view similar to FIG. 4 with the treatment catheter still in place and the marking catheter actuated to introduce a drop of dye into the heart wall proximate the channel.
Figure 7:
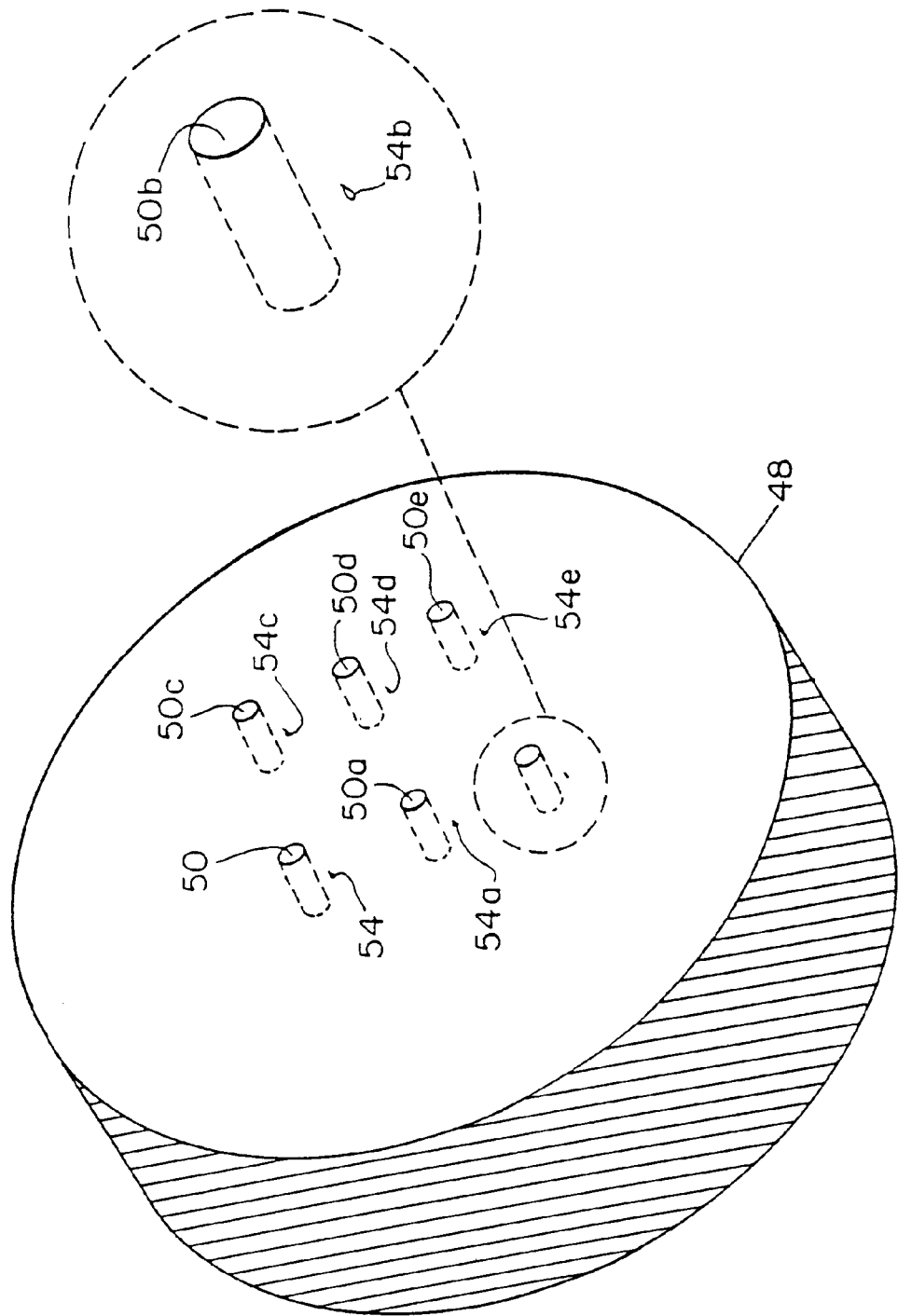
FIG. 7 is a diagrammatic three-dimensional view of a section of the heart wall showing a plurality of channels and adjacent markers.
Figure 8:
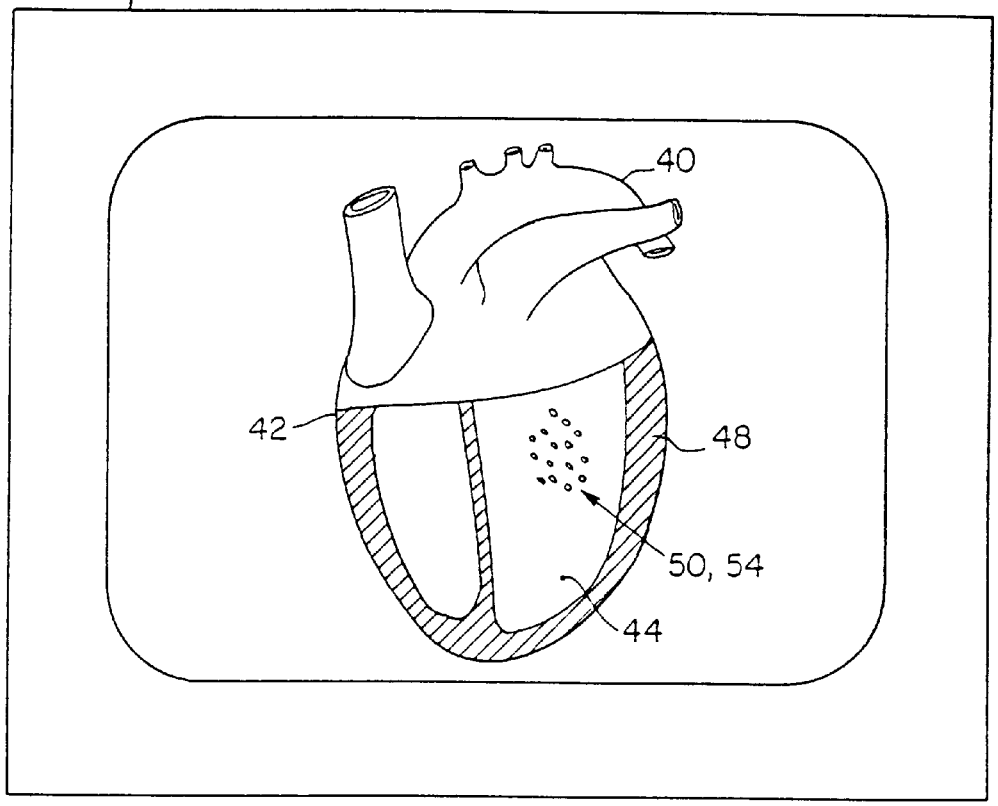
FIG. 8 illustrates a fluoroscopic image of a human heart displaying a number of markers indicating the position of channels in the heart wall.

With the tip 28 of treatment catheter 14 still resident in channel 50, FIG. 5, a needle or cannula 52 is extended from tip 30 of marking catheter 16 to inject a drop of imaging dye 54 into heart wall 48 proximate channel 50. This is accomplished by actuating plunger or piston 36 of syringe 32 so that a predetermined amount of fluid is forced out of cylinder or body 34 through conduit 38 through marking catheter 16 and out the end of needle 52. Subsequently, catheter system 12 is withdrawn from channel 50 leaving channel 50 simply marked by marker 54 made up of the radiopaque dye, for example. Dyes are temporary markers. For a more permanent mark a metal material may be used or a metal powder may be added to the dye. The radiopaque dye may be Renographin or an iodinated compound. Having seen where channel 50 is, as indicated by marker 54, the surgeon can now properly reposition the lens 28 at the tip of treatment catheter 14 at a new position on wall 48 spaced from channel 50 in preparation for the cutting of the next channel properly positioned and spaced with respect to channel 50 and all other channels previously cut and marked. After a number of such channels have been cut and marked the section of the heart wall 48 will appear as in FIG. 7, with each channel 50, 50a, 50b, 50c, 50d and 50e marked by imaging medium 54, 54a, 54b, 54c, 54d and 54e. The view seen by the surgeon on an electronic fluoroscope 60, FIG. 8, shows all of the imaging media 54 which mark the channels already cut into the heart wall. Utilizing this image the surgeon can properly locate and space the next channel to be created with respect to all the previous marked channels.

Although thus far the imaging medium has been explained in terms of a fluoroscopic dye, this is not a necessary limitation of the invention. It may be a radiopaque dye or any suitable material which can be seen using standard imaging techniques. For example, a metal staple or permanent suture 54', FIG. 9A, may be manipulated by clamp 72 in a conventional way for insertion into the heart wall 48, FIG. 9B, proximate channel 50'. In another configuration, a permanent suture 54", FIG. 10A, having barbs 82 at one end may be introduced via cannula 84 at the distal end of marker catheter 16b so that it becomes lodged in wall 48, FIG. 10B, next to channel 50" in heart wall 48. Sutures 54' or 54" may be made of any suitable material such as a radiopaque material, e.g., tantalum, platinum, gold, stainless steel.

In another alternative, cannula 90, FIG. 11, at the tip of marker catheter 16c is loaded with beads 54''' which may be metal or fluorescing material or radiopaque material. A train of beads 54''', FIG. 12, may be located in cannula 90 and as far back as desired in marker catheter 16c so that upon operation of plunger 36''' one or more beads 54''' will be dispensed by the piston 94 through the sharp end 96 of cannula 90 to be lodged in heart wall 48, FIG. 13. Gradations 97 in conjunction with the edge 99 of body 34''' allows dispensing of one or a selected number of beads 54'''.

Figure 14A:
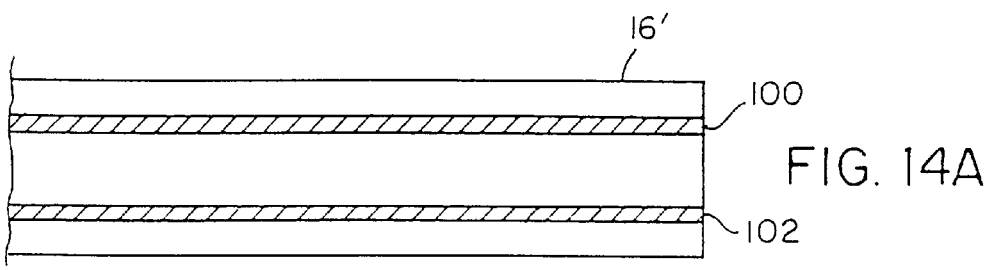
FIG. 14A is a side sectional view of a bipolar electrode tip for the treatment catheter.
Figure 14B:
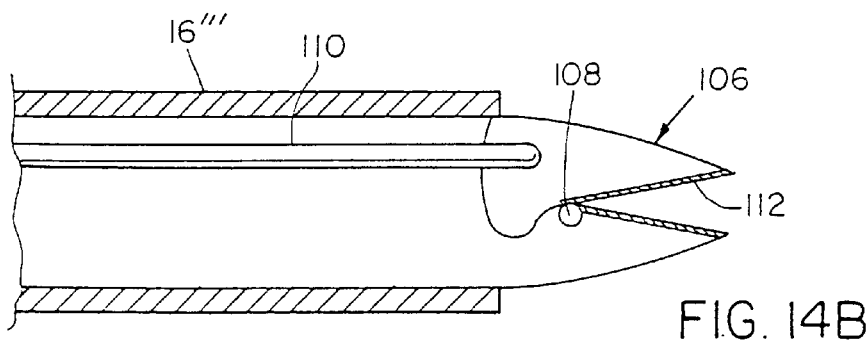
FIG. 14B is a view similar to FIG. 14A of the tip of the treatment catheter showing a scissor for ablating tissue.

Although thus far the invention has been disclosed in conjunction with an ablative device which uses laser energy conducted through a fiber optic element to produce the tissue ablation, this is not necessary. For example, as shown in FIG. 14A, the distal end of treatment catheter 16' may include a pair of conductors 100, 102 for providing an electric field across the tissue. In another construction, FIG. 14B, the distal end of treatment catheter 16''' may include scissors 106 pivoted at 108 with a control wire 110 attached to one of the jaws 112 and threaded back through catheter 16''' to the proximal end where it can be manipulated at control 22 to operate scissors 106.

Figure 3:
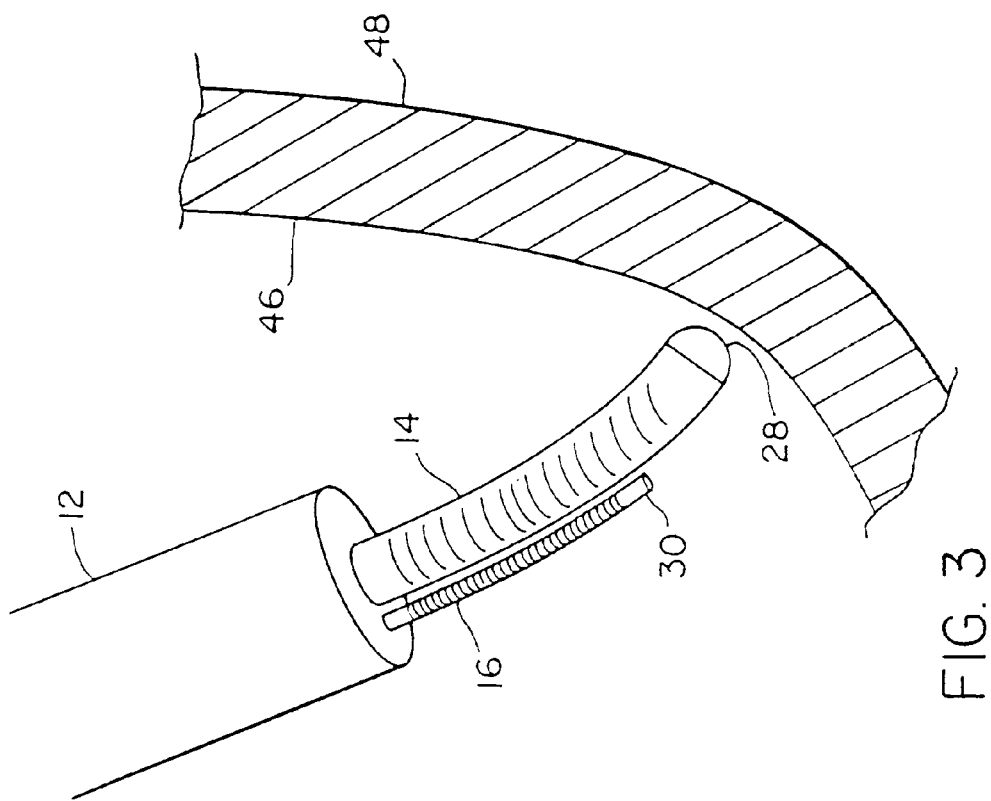
FIG. 3 is an enlarged detailed partially sectional view of a portion of the heart of FIG. 2 showing the treatment catheter in contact with the wall preparatory to application of the ablative energy.
Figure 6:
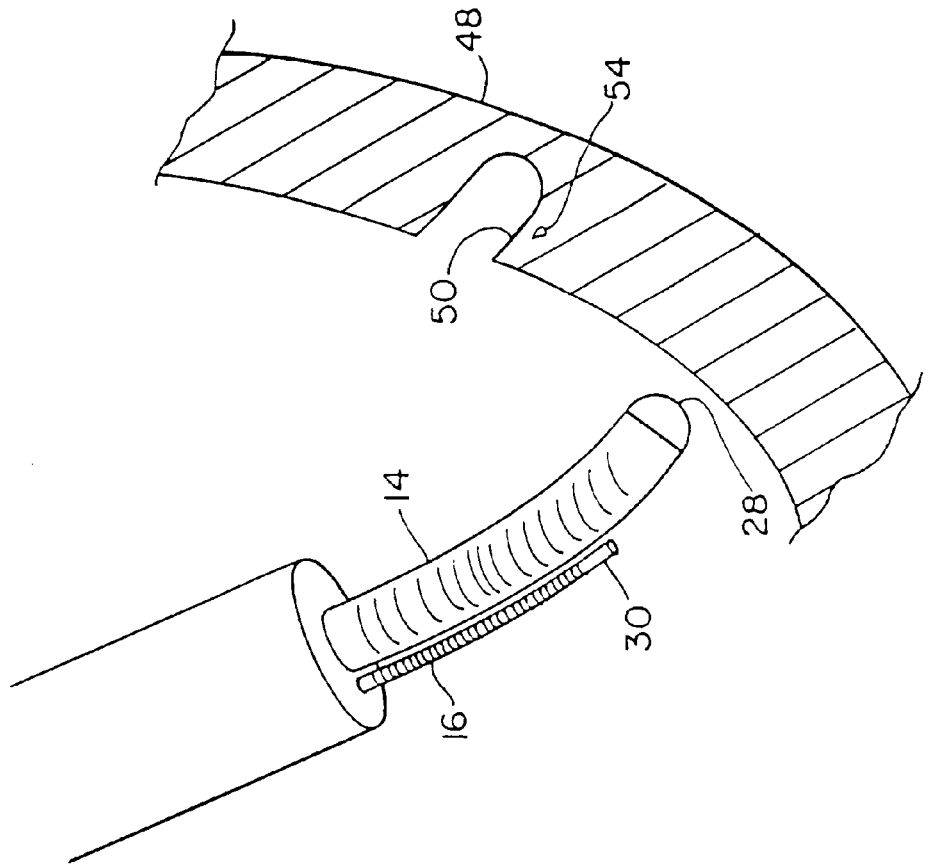
FIG. 6 is a view of the heart wall showing the channel and the marker after the catheter has been withdrawn and repositioned to make a subsequent channel.
Figure 15:
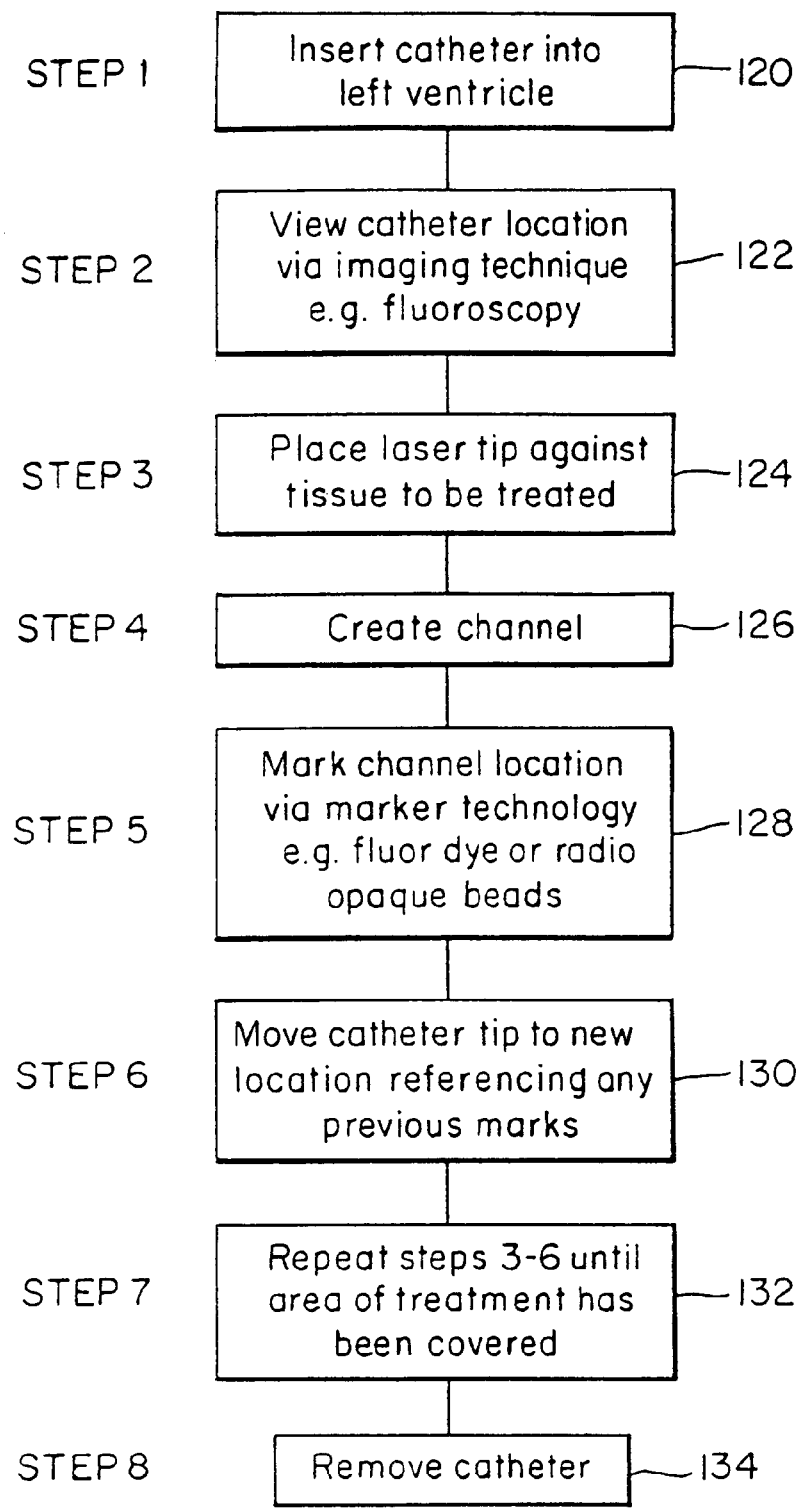
FIG. 15 depicts the steps and the method according to one embodiment of the method of this invention.

Channel marking is accomplished according to the method of this invention by inserting the catheter such as catheter system 12 into the left ventricle of the heart, step 120 of FIG. 15, and then viewing the catheter location on a fluoroscope, for example, step 122, as shown in FIG. 8. The laser tip is then placed against the tissue to be treated, step 124, as shown in FIG. 3, and the ablative energy, for example from laser 24, FIG. 1, is provided to ablate the target tissue, step 126. The channel is then marked step 128, as shown in FIG. 5, after which the catheter is removed, step 130, as shown in FIG. 6, leaving behind the newly created channel and its marker 54. These steps are done repeatedly, step 132, until the area of treatment has been covered with a predetermined pattern of properly located and spaced myocardial revascularization channels, after which the catheter is removed in step 134. The marker catheter may be made removable in order to replenish the supply of marking media such as beads, staples or dye without having to remove the treatment catheter.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. A method of marking a percutaneous transmyocardial revascularization channel comprising:

inserting a catheter into a chamber of a heart of a patient;

applying tissue ablative energy through said catheter to create a channel into the heart wall and then introducing to the heart wall proximate the channel for imaging; and viewing said imaging medium via an external imaging device positioned outside of said patient.

2. The method of claim 1 further including aiming the catheter at a new position of the heart wall spaced from all previously marked channels, applying tissue ablative energy through said catheter to create another channel into said heart wall and introducing to the heart wall proximate that channel an imaging medium for marking the position of that channel.

* * * * *

UNITED STATES PATENT AND TRADEMARK OFFICE
CERTIFICATE OF CORRECTION

PATENT NO. : 6,030,377
DATED : February 29, 2000
INVENTOR(S) : Linhares et al.

It is certified that error appears in the above-identified patent and that said Letters Patent is hereby corrected as shown below:

In claim 1, found in Col. 6, line 17, insert -- an imaging medium for marking the position of that channel -- after "channel".

Signed and Sealed this

Twenty-first Day of November, 2000

Attest:

Q. TODD DICKINSON

*Attesting Officer*  *Director of Patents and Trademarks*